United States Patent
Ponce

(10) Patent No.: US 6,494,204 B1
(45) Date of Patent: Dec. 17, 2002

(54) NASAL MEDICATION ADMINISTERING DEVICE

(76) Inventor: Pedro D. Ponce, 14621 NW. 3rd Ave., Miami, FL (US) 33168

( * ) Notice: Subject to any disclaimer, the term of this patent is extended or adjusted under 35 U.S.C. 154(b) by 103 days.

(21) Appl. No.: 09/602,039

(22) Filed: Jun. 23, 2000

(51) Int. Cl.[7] ............................................. A61M 15/08
(52) U.S. Cl. ........................ 128/203.22; 128/203.18; 128/203.22; 128/200.14; 128/207.18
(58) Field of Search ................. 128/200.14, 200.24, 128/203.12, 203.18, 203.22, 206.11, 207.18, 200.22, 203.23, 203.28, 204.11, 204.12, 204.13, 204.14; 604/94.01

(56) References Cited

U.S. PATENT DOCUMENTS

| | | | | |
|---|---|---|---|---|
| 1,155,608 A | * | 10/1915 | Nieschang | 128/203.22 |
| 1,540,274 A | * | 6/1925 | Moore | 128/203.22 |
| 2,052,321 A | * | 1/1936 | Smart | 601/148 |
| 3,502,078 A | * | 3/1970 | Hill | 604/212 |
| 3,666,182 A | * | 5/1972 | Cureton | 128/200.14 |
| 3,710,799 A | | 1/1973 | Caballero | |
| 4,226,848 A | | 10/1980 | Nagai et al. | |
| 4,955,945 A | * | 9/1990 | Weick | 128/203.12 |
| 5,116,311 A | * | 5/1992 | Lofstedt | 128/200.22 |
| 5,509,409 A | | 4/1996 | Weatherholt | |
| 5,546,929 A | | 8/1996 | Muchin | |
| 5,549,103 A | * | 8/1996 | Johnson | 128/200.24 |
| D379,513 S | | 5/1997 | Ierulli | |
| 5,666,948 A | * | 9/1997 | Matson | 128/200.23 |
| 5,706,800 A | | 1/1998 | Cronk et al. | |
| 5,735,272 A | | 4/1998 | Dillon et al. | |
| 6,093,169 A | * | 7/2000 | Cardoso | 128/207.18 |

* cited by examiner

Primary Examiner—Dennis Ruhl
Assistant Examiner—Michael G Mendoza

(57) ABSTRACT

A nasal medication administering device for providing a quick and easy way of safely administering medication to a user. The nasal medication administering device includes at least one flexible and squeezable medication-containing container; and also includes at least one flexible tubular member having an open first end and an open second end and a bore extending therethrough with the first end being extended through a wall of and into the medication-containing container and with the second end being adapted to be extended into a nasal passage of a user; and further includes at least one cap member being removably attached about the second end of the at least one flexible tubular member for closing the opening through the second end.

13 Claims, 4 Drawing Sheets

NASAL MEDICATION ADMINISTERING DEVICE

BACKGROUND OF THE INVENTION

1. Field of the Invention

The present invention relates to a disposable medication administering device and more particularly pertains to a new nasal medication administering device for providing a quick and easy way of safely administering medication to a user.

2. Description of the Prior Art

The use of a disposable medication administering device is known in the prior art. More specifically, a disposable medication administering device heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,735,272; U.S. Pat. No. 5,706,800; U.S. Pat. No. 5,546,929; U.S. Pat. No. 4,226,848; U.S. Pat. No. 5,509,409; and U.S. Pat. No. 3,710,799.

While these devices fulfill their respective, particular objectives and requirements, the aforementioned patents do not disclose a new nasal medication administering device. The inventive device includes at least one flexible and squeezable medication-containing container; and also includes at least one flexible tubular member having an open first end and an open second end and a bore extending therethrough with the first end being extended through a wall of and into the medication-containing container and with the second end being adapted to be extended into a nasal passage of a user; and further includes at least one cap member being removably attached about the second end of the at least one flexible tubular member for closing the opening through the second end.

In these respects, the nasal medication administering device according to the present invention substantially departs from the conventional concepts and designs of the prior art, and in so doing provides an apparatus primarily developed for the purpose of providing a quick and easy way of safely administering medication to a user.

SUMMARY OF THE INVENTION

In view of the foregoing disadvantages inherent in the known types of disposable medication administering device now present in the prior art, the present invention provides a new nasal medication administering device construction wherein the same can be utilized for providing a quick and easy way of safely administering medication to a user.

The general purpose of the present invention, which will be described subsequently in greater detail, is to provide a new nasal medication administering device which has many of the advantages of the disposable medication administering device mentioned heretofore and many novel features that result in a new nasal medication administering device which is not anticipated, rendered obvious, suggested, or even implied by any of the prior art disposable medication administering device, either alone or in any combination thereof.

To attain this, the present invention generally comprises at least one flexible and squeezable medication-containing container; and also includes at least one flexible tubular member having an open first end and an open second end and a bore extending therethrough with the first end being extended through a wall of and into the medication-containing container and with the second end being adapted to be extended into a nasal passage of a user; and further includes at least one cap member being removably attached about the second end of the at least one flexible tubular member for closing the opening through the second end.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new nasal medication administering device which has many of the advantages of the disposable medication administering device mentioned heretofore and many novel features that result in a new nasal medication administering device which is not anticipated, rendered obvious, suggested, or even implied by any of the prior art disposable medication administering device, either alone or in any combination thereof.

It is another object of the present invention to provide a new nasal medication administering device which may be easily and efficiently manufactured and marketed.

It is a further object of the present invention to provide a new nasal medication administering device which is of a durable and reliable construction.

An even further object of the present invention is to provide a new nasal medication administering device which is susceptible of a low cost of manufacture with regard to both materials and labor, and which accordingly is then susceptible of low prices of sale to the consuming public, thereby making such nasal medication administering device economically available to the buying public.

Still yet another object of the present invention is to provide a new nasal medication administering device which provides in the apparatuses and methods of the prior art some of the advantages thereof, while simultaneously overcoming some of the disadvantages normally associated therewith.

Still another object of the present invention is to provide a new nasal medication administering device for providing a quick and easy way of safely administering medication to a user.

Yet another object of the present invention is to provide a new nasal medication administering device which includes at least one flexible and squeezable medication-containing container; and also includes at least one flexible tubular member having an open first end and an open second end and a bore extending therethrough with the first end being extended through a wall of and into the medication-containing container and with the second end being adapted to be extended into a nasal passage of a user; and further includes at least one cap member being removably attached about the second end of the at least one flexible tubular member for closing the opening through the second end.

Still yet another object of the present invention is to provide a new nasal medication administering device that prevents germs and bacteria from being transmitted from person to another since each medication administering device contains one dosage for the user.

Even still another object of the present invention is to provide a new nasal medication administering device that safe and easy to administer the medication to the user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
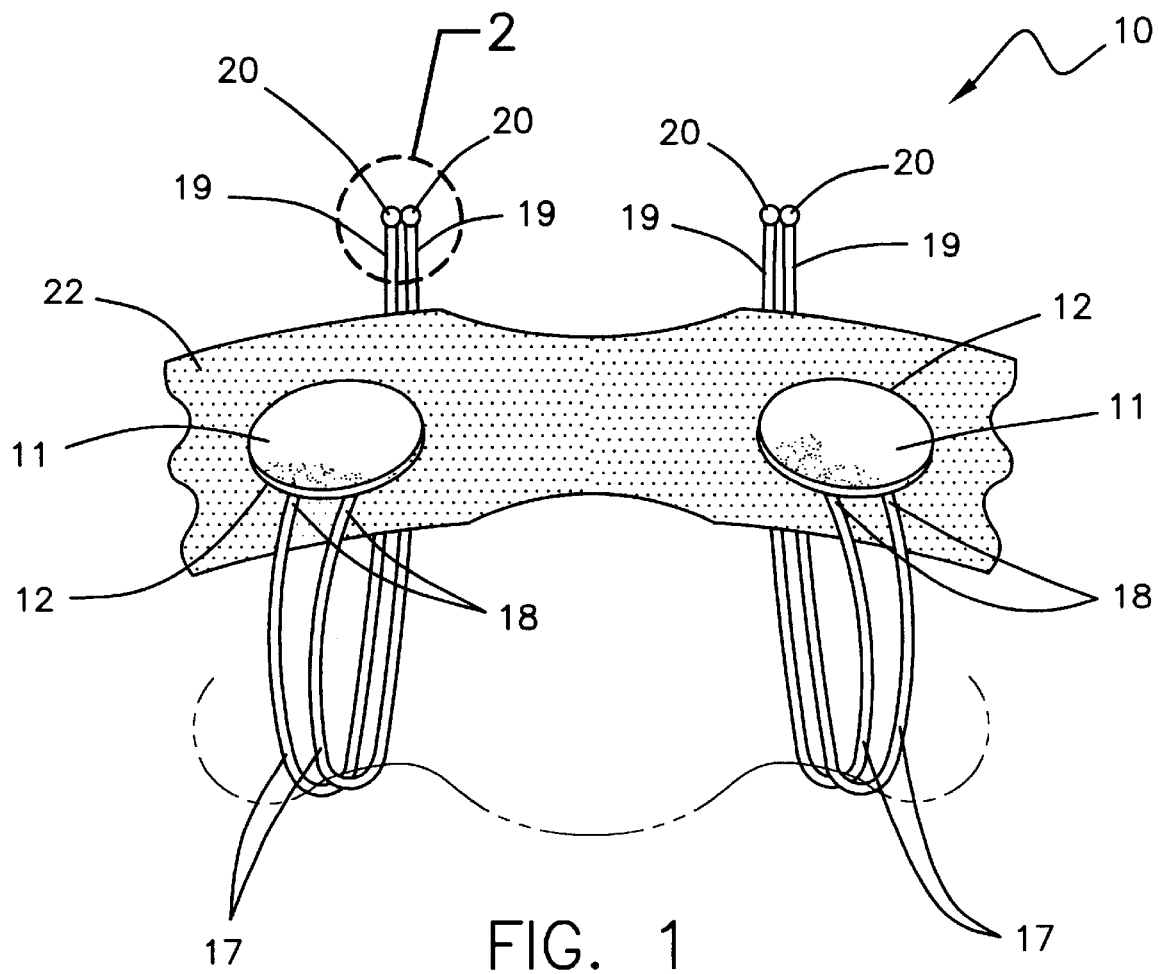
FIG. 1 is a perspective view of a first embodiment of a new nasal medication administering device according to the present invention.
Figure 2:
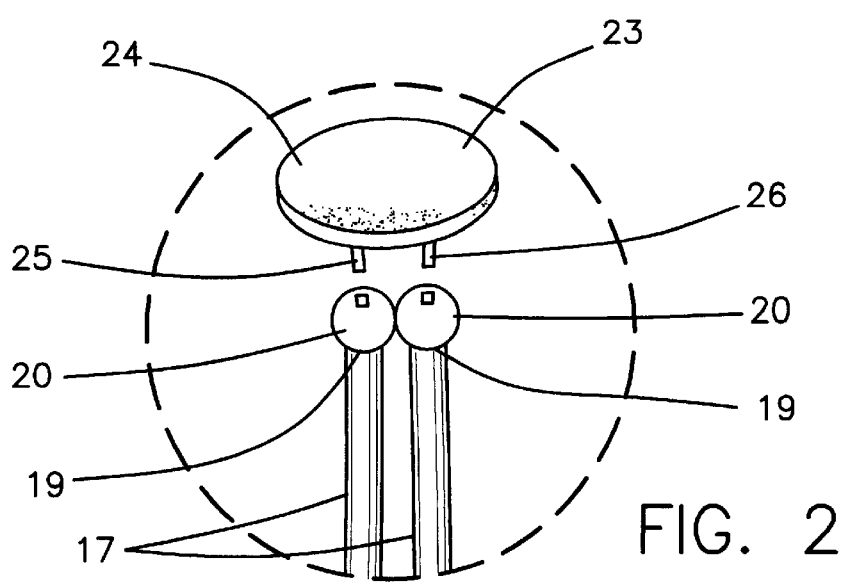
FIG. 2 is a perspective view of a first and second embodiments of the second ends of the flexible tube present invention.
Figure 3:
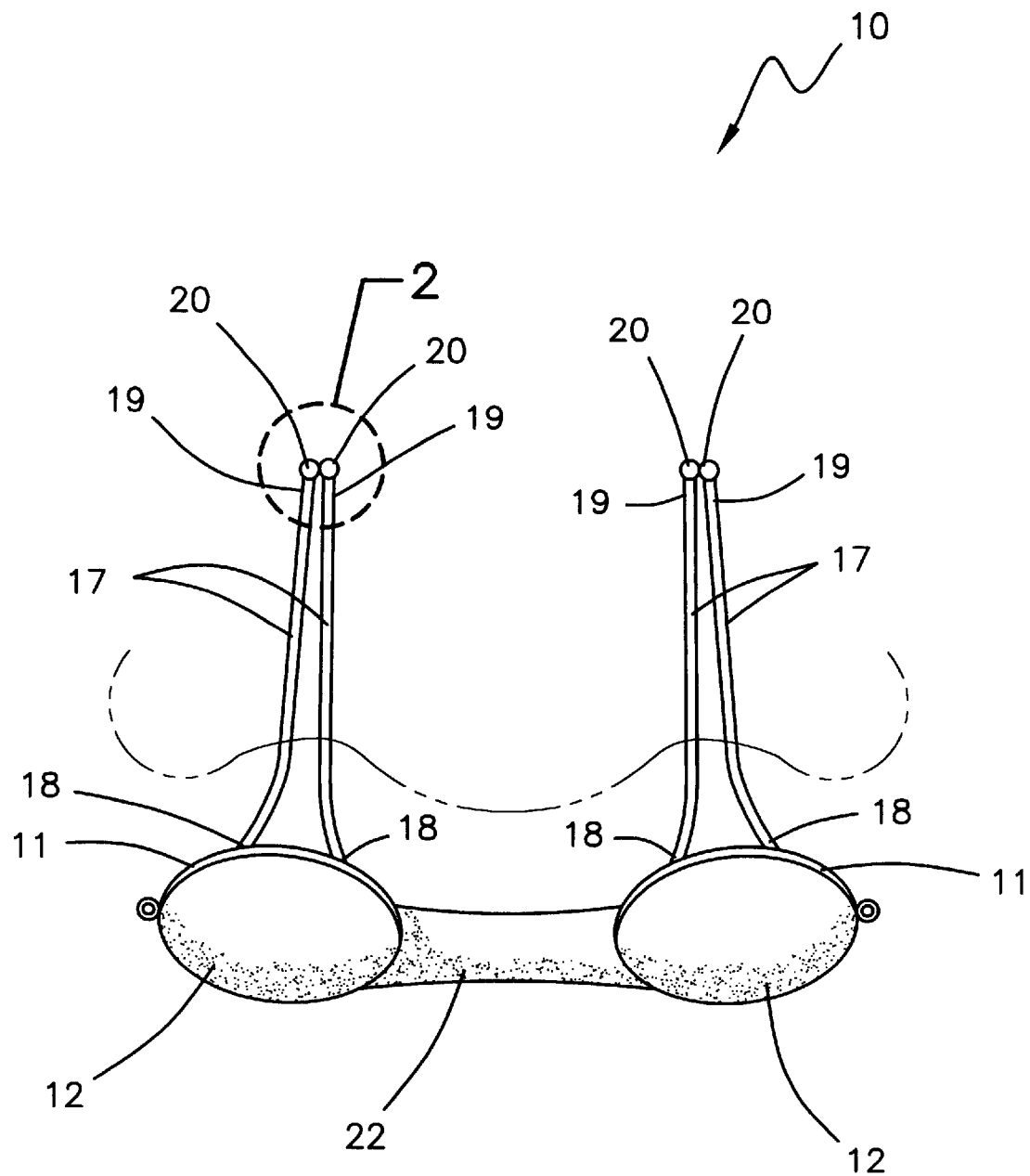
FIG. 3 is a perspective view of the second embodiment of the present invention.
Figure 4:
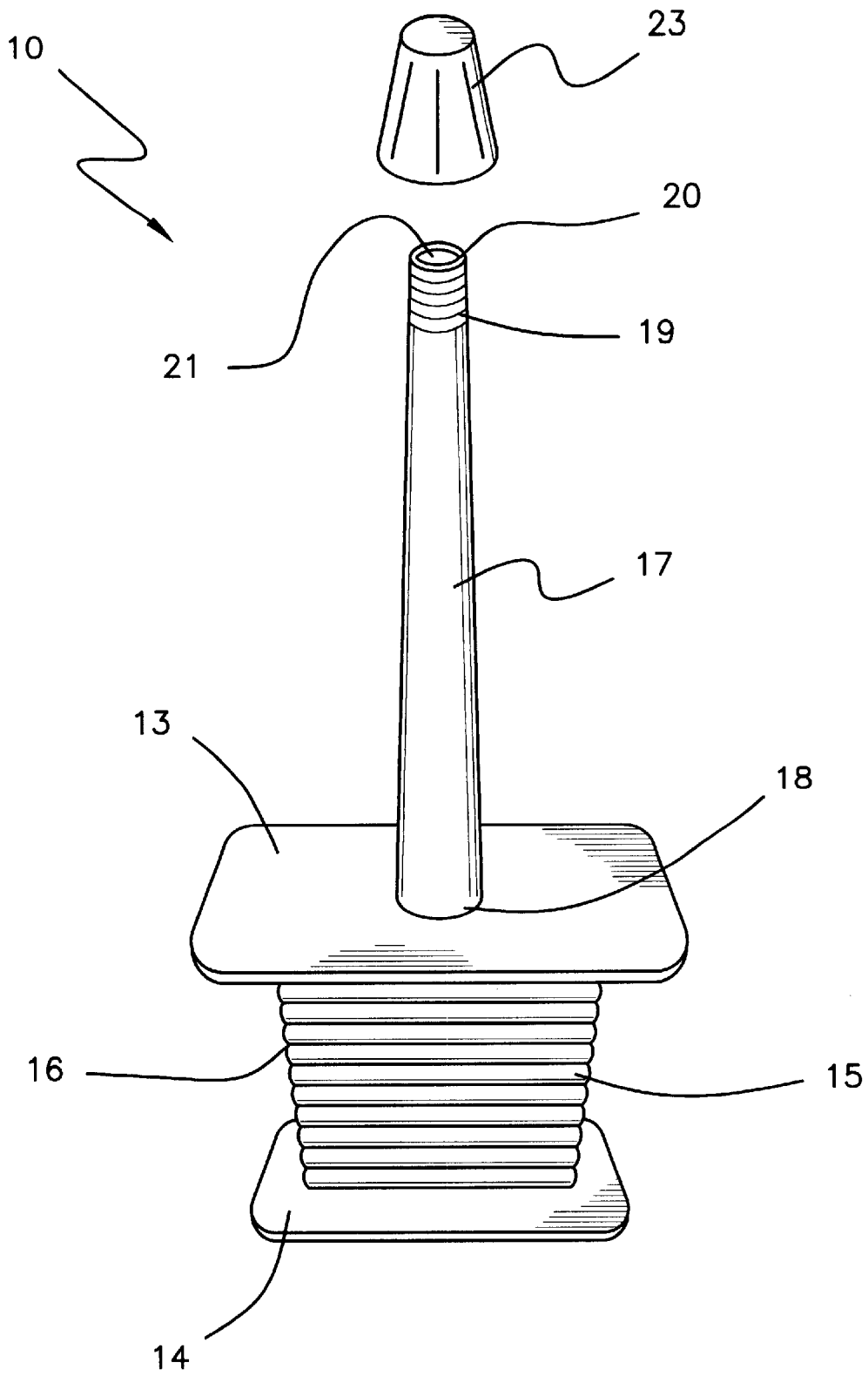
FIG. 4 is a perspective view of a third embodiment of the present invention.
Figure 5:
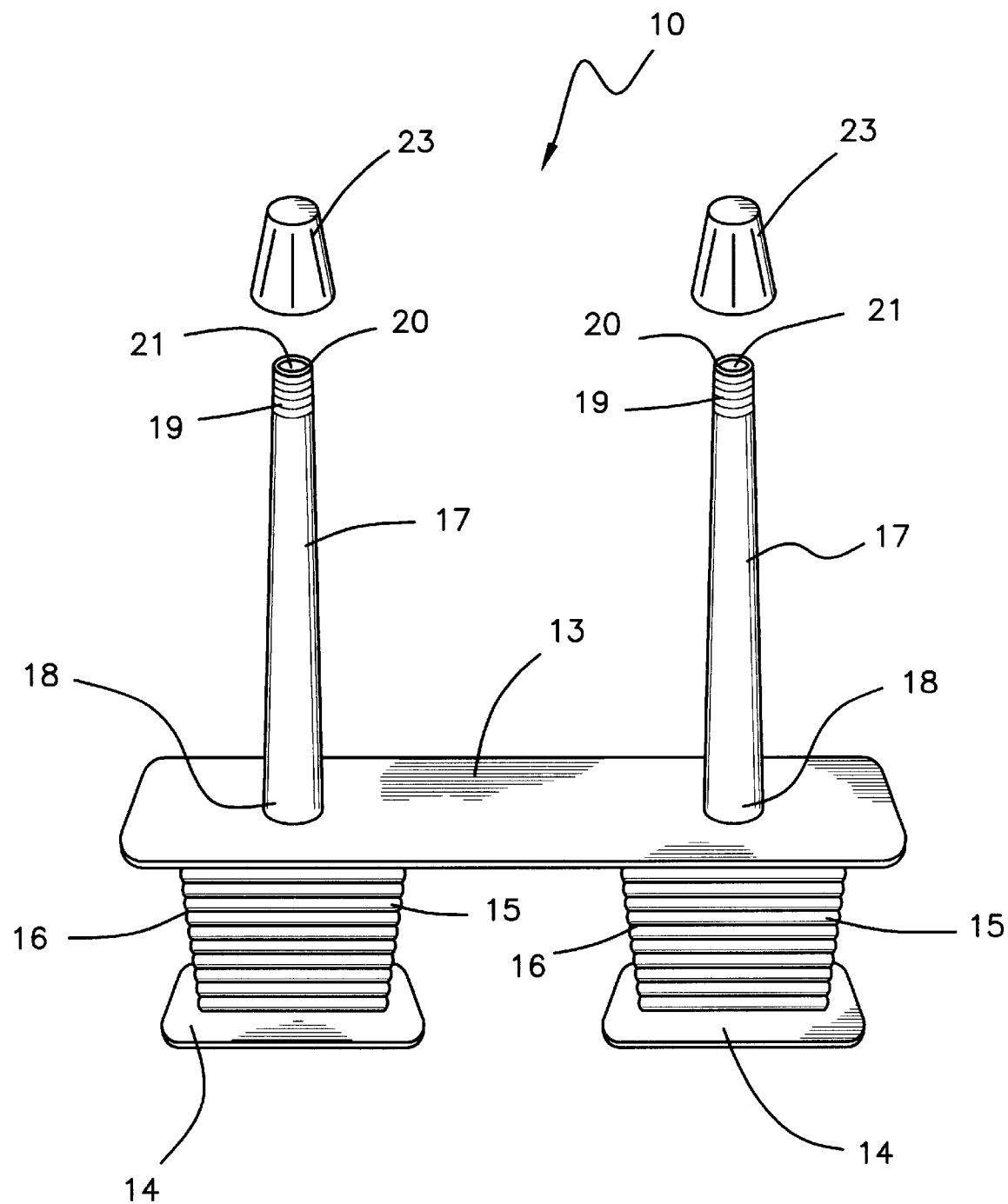
FIG. 5 is a perspective view of a fourth embodiment of the present invention.

With reference now to the drawings, and in particular to FIGS. 1 through 5 thereof, a new nasal medication administering device embodying the principles and concepts of the present invention and generally designated by the reference numeral 10 will be described.

As best illustrated in FIGS. 1 through 5, the nasal medication administering device 10 generally comprises at least one flexible and squeezable medication-containing container 11 which is adapted to contain one dosage of liquid medication; and also comprises at least one flexible tubular member 17 having a first end 18 with an opening therethrough and also having a second end 19 with an opening 20 therethrough and further having a bore 21 extending therethrough. The first end 18 is extended through a wall of and into the medication-containing container 11 and the second end 19 is adapted to be extended into a nasal passage of a user. At least one cap member 23 is removably attached about the second end 19 of the at least one flexible tubular member 17 for closing the opening 20 through the second end 19.

As a first and second embodiment, the wall of the at least one medication-containing container 11 includes a flexible membrane 12 for urging liquid medication into and through the at least one flexible tubular member 17 upon the flexible membrane 12 being squeezed. The at least one medication-containing container 11 includes a pair of the medication-containing containers 11 one for each nostril of a user. The medication-containing containers 11 are securely supported upon and interconnected with a strip of material 22. The at least one flexible tubular member 17 includes a plurality of the flexible tubular members 17 being securely connected to a respective medication-containing container 11. The at least one cap member 23 includes a pair of the cap members 23 each being removably attached to the second ends 19 of a respective pair of the flexible tubular members 17. Each cap member 23 includes a disc-like member 24 having tab-like plugs 25,26 being securely attached to and extending from the disc-like member 24 and being removably extended in the openings 20 of a respective pair of flexible tubular members 17 to essentially plug the openings 20 through the second ends 19 thereof. The difference essentially between the first and second embodiment is that the strip of material 22 in the first embodiment is adhesive tape 22 being adapted to applied to a nose of a user.

As a third embodiment, the at least one medication-containing container 11 includes a pair of tab-like members 13,14 being biasedly spaced apart with a spring member 15 being securely and conventionally attached to and being disposed between the tab-like members 13,14 and with a flexible membrane 16 being encircled about the spring member 15 and being securely and conventionally attached to the tab-like members 13,14 and being adapted to contain liquid medication therein. The at least one cap member 23 is adapted to thread upon the second end 19 of the at least one flexible tubular member 17 to essentially close the opening 20 therethrough.

As a fourth embodiment, the at least one medication-containing container 11 includes a pair of the medication-containing containers 11 one for each nostril. Each of the medication-containing containers 11 has a first 13 and second 14 tab-like members being biasedly spaced apart with a spring member 15 being securely and conventionally attached to and being disposed between the tab-like members 13,14 and with a flexible membrane 16 being encircled about the spring member 15 and being securely and conventionally attached to the tab-like members 13,14 and being adapted to contain liquid medication therein. The first tab-like member 13 is common to both the medication-containing containers 11. The at least one flexible tubular member 17 includes a pair of flexible tubular members 17 each having the first end 18 being securely attached to and extended in a respective medication-containing container 11. The at least one cap member 23 includes a pair of cap members 23 each being threaded upon the second end 19 of a respective flexible tubular member 17 for closing the opening 19 therethrough.

In use, the user removes the cap member(s) 23 from the second end(s) 19 of the flexible tubular member(s) 17 and extends the second end(s) 19 into one's nostrils and squeezes upon either the flexible membrane 12 or the tab-like members 13,14 to urge the liquid medication from the medication-containing container(s) 11 into the nostrils through the flexible tubular member(s) 17. When finished, the user simply disposes of the medication administering device 10.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A nasal medication administering device comprising:
   at least one flexible and squeezable medication-containing container, said container being positionable against an outer surface of a nose of a user;
   an attachment means for releasably attaching said container to the outer surface of the nose of the user, said attachment means being mounted to said container and being positioned between the outer surface of the nose and the container when attached to the outer surface of the nose such that said container is unobstructed by said attachment means;
   at least one flexible tubular member having an open first end and an open second end and a bore extending therethrough, said first end being extended through a wall of and into said medication-containing container, said second end being adapted to be extended into a nasal passage of a user; and
   at least one cap member being removably couplable to said second end of said tubular member for closing said open second end.

2. A nasal medication administering device as described in claim 1, wherein said container is adapted to contain one dosage of liquid medication.

3. A nasal medication administering device as described in claim 1, wherein said wall of said container includes a flexible membrane for urging liquid medication into and through said tubular member upon said flexible membrane being squeezed.

4. A nasal medication administering device as described in claim 1, wherein said attachment means comprises an elongate flexible adhesive tape material.

5. A nasal medication administering device as described in claim 1, wherein said container is disc-shaped and has a substantially flat profile to lie flatly on the nose of the user in an unobtrusive visual manner and to facilitate pinching of said container against the outer surface of the nose to administer the medication.

6. A nasal medication administering device as described in claim 1, wherein said at least one medication-containing container includes a pair of said medication-containing containers one for each nostril of the user.

7. A nasal medication administering device as described in claim 6, wherein said at least one flexible tubular member includes a pair of said flexible tubular members being securely connected to a respective one of said medication-containing containers.

8. A nasal medication administering device as described in claim 7, wherein said at least one cap member includes a pair of said cap members each being removably attached to said second ends of a said pair of said flexible tubular members.

9. A nasal medication administering device as described in claim 8, wherein each of said cap members comprises a main portion having a pair of plugs being securely attached to and extending away from said main portion and being removably positionable in said openings of a respective one of said pair of said flexible tubular members to essentially plug said openings through said second ends.

10. A nasal medication administering device as described in claim 7, wherein each of said containers are spaced apart when mounted to said attachment means to facilitate the positioning of each of said pairs of tubular members in a respective one of the nostrils of the user when said attachment means is positioned on the nose of the user.

11. A nasal medication administering device as described in claim 7, wherein each of said ends of said pairs of tubular members being coupled together to restrict each of said tubular members of said pair of tubular members from being inserted into separate nostrils.

12. A nasal medication administering device as described in claim 7, wherein each of said ends of said pairs of tubular members being coupled together to permit the passage of medication from said container through at least one of said pair of tubular members if an adjoining said tubular member becomes blocked.

13. A nasal medication administering device comprising:
   at least one flexible and squeezable medication-containing container, said container being positionable against an outer surface of a nose of a user;
   an attachment means for releasably attaching said container to the outer surface of the nose of the user, said attachment means being mounted to said container and being positioned between the outer surface of the nose and the container when attached to the outer surface of the nose such that said container is unobstructed by said attachment means;
   at least one flexible tubular member having an open first end and an open second end and a bore extending therethrough, said first end being extended through a wall of and into said medication-containing container, said second end being adapted to be extended into a nasal passage of a user;
   at least one cap member being removably couplable to said second end of said tubular member for closing said open second end; nose of the user;
   wherein each of said ends of said pairs of tubular members being coupled together to restrict each of said tubular members of said pair of tubular members from being inserted into separate nostrils; and
   wherein each of said ends of said pairs of tubular members being coupled together to permit the passage of medication from said container through at least one of said pair of tubular members if an adjoining said tubular member becomes blocked.

* * * * *